United States Patent [19]

Chumak et al.

[11] Patent Number: 5,368,166

[45] Date of Patent: * Nov. 29, 1994

[54] DEVICE FOR AUTOMATICALLY CONTROLLING THE PROCESS OF SEPARATING FROTH CONCENTRATE FROM GANGUE IN A FLOATATION MACHINE

[76] Inventors: Fedor A. Chumak, Novy gorod, 6, kv.50., Udachny-1; Vladimir N. Cherednik, Ulitsa Lenina,20,kv.16.; Mikhail N. Zlobin, ulitsa Pavlova,12,kv.1., both of Mirny, all of U.S.S.R.

[ * ] Notice: The portion of the term of this patent subsequent to Apr. 29, 2009 has been disclaimed.

[21] Appl. No.: 586,261

[22] Filed: Sep. 21, 1990

[51] Int. Cl.[5] .......................... B03D 1/00; B03D 1/02
[52] U.S. Cl. ........................ 209/168; 209/164; 209/166; 209/1
[58] Field of Search ............ 209/1, 164, 166, 167, 209/168, 169, 170

[56] References Cited

U.S. PATENT DOCUMENTS

| | | | |
|---|---|---|---|
| 3,551,897 | 12/1970 | Cooper | 209/166 |
| 3,747,902 | 10/1969 | Putman | 209/166 |
| 4,552,651 | 11/1985 | Sandbrook | 209/166 |

FOREIGN PATENT DOCUMENTS

| | | | |
|---|---|---|---|
| 2180779 | 4/1987 | United Kingdom | 209/166 |
| 662150 | 2/1978 | U.S.S.R. | 209/166 |

OTHER PUBLICATIONS

"Systemy automaticheskogo kontrolya i upravlenia tekhnologicheskimi protsessami flotatsionnykh ustanovok" by Kovin et al, Nedra Publishers, Moscow 1981 (pp. 69–73) (no translation).

Primary Examiner—Stanley S. Silverman
Assistant Examiner—Thomas M. Lithgow

[57] ABSTRACT

The automatic control device comprises a channel used to measure the level and density of pulp in a chamber of a floatation machine, in which two bubbling tubes communicate with a differential pressure transducer connected to the input of a frother flow control channel and to the input of a correction unit whose other input is connected to a pressure transducer communicating with one of the bubbling tubes. The bubbling tubes are installed in hydrostatic tubes located outside the chamber and communicating therewith at different levels relative to the pulp level. The output of the correction unit is connected to the input of a circuit designed to control the flow rate of water and frother in a pulp level stabilizing channel and having its output connected to an actuator valve of a pipeline feeding water and frother. A water and frother flow transducer is connected to the input of a circuit designed to control the gangue discharge rate in the pulp level stabilizing channel and having its output connected to the drive of an actuator valve of a branch pipe used to discharge gangue.

19 Claims, 3 Drawing Sheets

DEVICE FOR AUTOMATICALLY CONTROLLING THE PROCESS OF SEPARATING FROTH CONCENTRATE FROM GANGUE IN A FLOATATION MACHINE

FIELD OF THE INVENTION

The present invention relates to concentration of minerals involving floatation of hard particles of a useful contrituent, more particularly, to a device for controlling automatically the process of separating froth concentrate from gangue in a floatation machine.

The invention can be advantageously used in ferrous and nonferrous metallurgy, coal mining and diamond industry to effect flotation of mineral resources, in which a valuable constituent represents fairly small or large inclusions possessing hydrophobic properties.

BACKGROUND ART

In prior art floatation machines, the process of separating froth concentrate from gangue involves either froth floatation, in which the source feed is pulp containing small fractions of the material to be concentrated, or froth floatation combined with froth separation, in which the source feed contains both small and large fractions of the material to be concentrated, the latter fraction being supplied into the froth layer. Froth floatation and a combination of froth floatation and froth separation are characterized by the need to monitor to a high accuracy the level and density of pulp in a chamber of a floatation machine since high control quality is difficult to attain unless the above parameters are accurately measured for a measurement error is automatically included into a static error in control operations. Furthermore, other necessary conditions are as follows: maintaining a predetermined pulp level in a chamber of a floatation machine with respect to its overflow threshold, thereby maintaining the pulp-froth layer interface and the thickness of the froth layer at a predetermined level, ensuring a desired liquid-to-gas phase ratio in the pulp supplied into a chamber of a floatation machine, the density and level of the pulp in the chamber being primarily determined by said ratio, maintaining optimal concentration in aerated pulp of frother supplied with circulating water and directly with the source feed, said parameter determining the size, degree of dispersion and the rise rate of air bubbles and, in effect, the density of aerated pulp; providing an optimal rate in supplying the source feed into the bulk of aerated pulp in a chamber of a floatation machine, changes in said rate impairing hydrodynamic characteristics of flows; discharging gangue from the chamber with minimum losses of the pulp liquid phase; and density of the pulp in the chamber.

Changes in the pulp level and, consequently, in the froth layer and also in the ratios between the solid, liquid and gas phases of the pulp are associated, firstly, with varying amounts of the source solid and water in the chamber of a floatation machine and, secondly, with varying losses of the liquid phase in discharging gangue due to changes in the quantity of the solid and in the content of large and heavy fractions therein. A change in the pulp level in the chamber of a floatation machine is also dependent on variations of the pulp density caused by a change in frother concentration in the pulp.

A change in the rate of feeding the pulp to the chamber of a floatation machine is caused by a variation of the solid-to-water ratio in the pulp. Thus, the disturbing factors affecting the froth floatation process are a change in the quantity of the solid and liquid phases of the pulp supplied to the chamber of a floatation machine, a change in the quantity of the liquid phase lost in unloading gangue due to a varying content of large and heavy fractions in gangue, a change in frother concentration in circulating water supplied to the chamber, which causes a variation of the liquid-to-gas phase ratio in the pulp and, in effect, variations of the pulp level and density in the chamber of a floatation machine.

From the aforesaid it follows that at the preset time quality control of the processes of froth floatation and froth floatation combined with froth separation presents an important connected with interrelated control of several parameters. This problem is particularly acute in the case of high-capacity floatation machines due to great sluggishness of a floatation installation comprising such machines and also because of major disturbing factors of different character.

The above problem is partially solved in a known device for controlling automatically the process of separating froth concentrate from gangue in a floatation machine (cf. G. M. Kovin et al: "Systemi avtomaticheskogo kontrolia i upravlenia teckhologicheskimi protsessami flotatsionnikh ustanovok", 1981, "Nedra" publishers, Moscow, pp. 69–73), which comprises a pulp level measuring circuit wherein a bubbling tube disposed in a chamber of a floatation machine communicates with a pressure transducer and an air flow governor. The output of the pressure transducer is connected to a pulp level recorder and to the input of a circuit designed to control the rate of unloading gangue from the chamber of the floatation machine and having its output connected to the drive of a control valve arranged on a branch pipe used to unload gangue from the chamber of the floatation machine. The foregoing device also includes a frother flow control circuit, in which the frother flow is controlled in proportion to the flow of gangue discharged from the chamber as pulp.

The disclosed automatic control device fails to provide for desired control quality due to the fact that, in measuring the pulp level in the chamber of the floatation machine, no account is taken of the error caused by changes in the pulp density, and also as a consequence of low accuracy in pulp level measurements. Its low accuracy in measurements is attributable to the presence of a constant component dependent on the depth of immersion of the bubbling tube in the pulp in the signal proportional to the pulp level. The above disadvantage is also associated with the fact that the bubbling tube is placed directly in the pulp, a factor leading to clogging of the bubbling tube in its lower portion and, in effect, distorting the measurement results and introducing an additional error.

The metering of the frother flow with respect to the flow of gangue discharged as pulp in the absence of pulp density monitoring is very approximate and impairs froth formation and hydrodynamic conditions in the chamber due to great variations of the pulp density, which generally hinders pulp level stabilization. Moreover, the absence of such a control action as water and frother flow stabilization during the floatation process makes more difficult the pulp level stabilization process.

The foregoing automatic control device does not ensure required control quality, particularly in high-capacity floatation machines due to severe disturbances and great sluggishness of floatation installations comprising such machines.

The above problem is partially solved in another known device for controlling automatically the process of separating froth concentrate from gangue in a floatation machine (cf. GB, A, 2180779), which comprises a channel used to measure the level and density of pulp in a chamber of a floatation machine, wherein two bubbling tubes installed at different levels in the pulp in the chamber of the floatation machine communicate with air flow governors and a differential pressure transducer connected to the input of a channel used to control the flow of frother supplied to the chamber of the floatation machine and to a first data input of a pulp level correction unit whose second data input is connected to a pressure transducer communicating with one of the bubbling tubes, while its output is connected to the input of a channel used to stabilize the pulp level in the chamber of the floatation machine, its circuit designed to control the rate of discharging gangue from the chamber of the floatation machine being connected to the drive of a gangue discharge valve placed on a branch pipe used to discharge gangue from the chamber of the floatation machine.

Similarly to the previously described device, the last-mentioned automatic control device fails to provide for desired control quality. This disadvantage is attributable to the fact that pulp level stabilization solely by changing the rate of gangue discharge from the chamber of the floatation machine is generally inefficient, particularly in the case of high-capacity floatation machines due to such factors as great sluggishness of floatation installations comprising such machines, the presence of strong disturbances and insufficient power in effecting control required to rapidly restore the pulp level to a predetermined value. A mere increase in the gain of the pulp level stabilizing channel with great disturbances will cause system driving, overcontrol and longer corrective action, due to which control quality will be adversely affected. The use of a more powerful actuator valve for discharging gangue from the chamber of a high-capacity floatation machine would increase its own sluggishness and, in effect, the sluggishness of a floatation installation comprising such a machine and automatic control means, and impair the control characteristics.

The aforesaid automatic control device is also incapable of ensuring the required control quality due to low accuracy in measuring the pulp density and, consequently, the pulp level in the chamber of a floatation machine since the pulp level is corrected with respect to the pulp density and the error occurring in measurements of the pulp level and density is automatically included into a static error in control operations, the former error being caused by the above factors.

In the foregoing automatic control device the rate of gangue discharge from the chamber of the floatation machine is changed by the use of an actuator valve having a nonlinear flow characteristic, which does not provide for desired control quality. Such an actuator valve fails to ensure maximum free discharge of gangue from the chamber of the floatation machine with minimum losses of the pulp liquid phase, which likewise results in disturbances as regards the pulp level in the chamber or the floatation machine. A vertical position of the above actuator valve (a horizontal position of the seat of the shut-off element) may result in partial or full clogging of the branch pipe used to discharge gangue from the chamber of the floatation machine in floatation of ore containing many large and heavy fractions and, consequently, bring about a change (decrease) in the rate of gangue discharge and additional disturbances as regards the pulp level in the chamber of the floatation machine, a feature further decreasing the control quality.

The floatation machine is known to use circulating water, in which residual frother concentration is as great as 70 to 80% of the working concentration. Changes occur in the flow of said circulating water with the source feed supplied to the chamber of the floatation machine and in losses occurring while gangue is discharged from the chamber of the floatation machine. This changes the pulp level and density, and also the hydrodynamic characteristics of the pulp flowing in the chamber of the floatation machine. Hence, maintaining the working frother concentration in the pulp in the chamber of the floatation machine merely by changing the additional feed of frother to the chamber of the floatation machine without stabilization of the flow of water and frother fails to provide, on the one hand, sufficient stabilization of water-to-air ratios in the bulk of aerated pulp and, in effect, of the pulp density and level and, on the other hand, a stable rate of supplying the source feed into the chamber of the floatation machine and, consequently, stable hydrodynamic characteristics of pulp flows in the chamber of the floatation machine.

BRIEF DESCRIPTION OF THE INVENTION

It is, therefore, an object of the present invention to provide a device for controlling automatically the process of separating froth concentrate from gangue in a floatation machine, which would improve control quality.

The foregoing object is accomplished by that a device for controlling automatically the process of separating froth concentrate from gangue in a floatation machine whose chamber is provided with a gangue discharge branch pipe and communicates via a source feed pipeline for a source feed and an aerated liquid" with a frother meter and a pipeline feeding water and frother comprises:

a channel used to measure the level and density of pulp in a chamber of a floatation machine and having first and second outputs;

first and second hydrostatic tubes in said pulp level and density measuring channel, installed outside said chamber of the floatation machine and communicating with said chamber at different levels relative to the pulp level;

a fluid source communicating with said hydrostatic tubes, the fluid having a known constant density and supplied into said hydrostatic tubes with an essentially constant flow rate;

first and second bubbling tubes in said pulp level and density measuring channel, placed in said hydrostatic tubes at different levels relative to the pulp level, which define a predetermined pulp level and density measurement range;

first and second air flow governors in said pulp level and density measuring channel, communicating with the first and second bubbling tubes, respectively;

a differential pressure transducer in said pulp level and density measuring channel, communicating with the first and second bubbling tubes and having an output serving as the first output of said pulp level and density measuring channel, which produces a signal corresponding to a pulp density increment;

a pressure transducer in said pulp level and density measuring channel, communicating with the first bubbling tube and having an output;

a pulp level correction unit in said pulp level and density measuring channel, having first and second data inputs and an output and connected via its first and second data inputs to said outputs of said pressure transducer and said differential pressure transducer, said output of said correction unit serving as the second output of said pulp level and density measuring channel, which produces a signal corresponding to a value of pulp level increment corrected with respect to density.

a channel used to control the flow of frother supplied into said chamber of the floatation machine, which has an input and an output and is connected via said input to the first output of said pulp level and density measuring channel and via said output to said frother meter;

a channel used to stabilize the pulp level in said chamber of the floatation machine, having first and second inputs and first and second outputs, a circuit designed to control the flow rate of water and frother supplied into said chamber, having an input serving as the first input of said pulp level stabilizing channel connected to the second output of said pulp level and density measuring channel, and an output serving as the first output of said pulp level stabilizing channel; a circuit designed to control the rate of gangue discharge from the chamber of the floatation machine, having an input and an output serving, respectively, as the second input of said pulp level stabilizing channel and its second output;

a first actuator valve installed on said pipeline feeding water and frother to the chamber of the floatation machine, having an input connected to the first output of said pulp level stabilizing channel, which produces a first control signal in response to deviation of pulp level increment from a preset value;

a second actuator valve used to discharge gangue and installed on said branch pipe for discharging gangue from the chamber of the floatation machine;

a drive of the second gangue discharge actuator valve, having an input connected to the second output of said pulp level stabilizing channel; and a water and frother flow transducer installed on said pipeline feeding water and frother and having an output connected to the second input of said pulp level stabilizing channel, which develops at its second output a second control signal fed to said drive of the second gangue discharge actuator valve in response to deviation of the flow rate of water and frother from a preset value.

It is advantageous that in the automatic control device according to the invention the pulp level correction unit should comprise a first current-to-voltage converter receiving at its input a signal corresponding to a pulp level increment relative to a minimum value, a second current-to-voltage converter receiving at its input a signal corresponding to a pulp density increment relative to a minimum value, a first multiplier unit having its input connected to the output of the second current-to-voltage converter and multiplying relevant data into a factor inversely proportional to the difference between the levels at which the hydrostatic tubes communicate with the chamber of the floatation machine, a second multiplier unit having its input connected to the output of the first multiplier unit and multiplying relevant data into a factor proportional to a minimum pulp level, a first adder having its first input connected to the output of the first current-to-voltage converter and its second input connected to the output of the second multiplier unit, a second adder having its first input connected to the output of the first multiplier unit and receiving at its second input a signal corresponding to a minimum pulp density value, a first divider unit having its input connected to the output of the second adder and dividing relevant data by a scale factor, a second divider unit having its first input connected to the output of the first divider unit and its second input connected to the output of the first adder, and a voltage-to-current converter whose input is connected to the output of the second divider unit.

It is also advantageous that in the automatic control device according to the invention the circuit designed to control the flow rate of water and frother supplied into said chamber should include a pulp level increment control, a circuit designed for comparing a corrected value of pulp level increment with a preset value and connected via its first input to the output of said pulp level increment control, and a water and frother flow governor whose input is connected to the output of the circuit designed for comparing a corrected value of pulp level increment with a preset value.

It is further advantageous that in the automatic control device according to the invention the gangue discharge actuator valve comprising a cylindrical case provided with an outlet, having on one of its ends a flange for connection with the branch pipe used to discharge gangue from the chamber of the floatation machine and mounting a seat and a shut-off member fitted with a rod for connection with the drive of the gangue discharge actuator valve should be characterized by that said cylindrical case is arranged in a substantially horizontal position, said outlet is provided in the lower portion of said case, and the shut-off member includes a cylindrical portion and a parabolic cone portion connected therewith and facing the seat, its axis being misaligned relative to the axis of a hole in the seat towards the upper portion of the cylindrical case.

It is preferable that in the proposed automatic control device the cross-sectional area of the cylindrical portion of the shut-off member should be determined as $$S=(l-k)S_n$$

where
S is the cross-sectional area of the cylindrical portion;
$S_n$ is the area of the hole in the seat; and
k is a proportionality factor equal to the ratio of a minimum load of the floatation machine to its maximum load, while the length of the parabolic cone portion is equal to the travel length of the drive of the gangue discharge actuator valve.

It is also preferable that in the proposed automatic control device the misalignment of the axis of the shut-off member relative to the axis of the hole in the seat should be equal to the difference between the radii of the cylindrical portion of the shut-off member and the hole in the seat.

It is further preferable that in the proposed automatic control device the shut-off member of the gangue discharge actuator valve should be provided with a pulp deflector placed on the end of its cylindrical portion.

In the automatic control device forming the subject of the present invention the pulp deflector desirably represents a disk with an annular depression on its lateral surface.

In addition to the circuit designed to control the rate of gangue discharge from the chamber of the floatation machine, the pulp level stabilizing channel of the proposed automatic control device comprises a circuit designed to control the flow rate of water and frother supplied into said chamber, which is used to effect an additional control by changing the flow rate of water and frother and subsequently stabilizing this flow rate.

The changing of the flow rate of water and frother supplied into the chamber is the second action intensifying the previous action involving a variation of the rate of gangue discharge from the chamber of the floatation machine with a view to accelerating the process of stabilizing the pulp level in the chamber. This decreases a maximum deviation of the pulp level in the chamber of the floatation machine from a preset value and, at the same time, reduces the pulp level control time from the moment a level deviation occurs to the instant the pulp level reaches a preset value.

Following a change in the flow rate of water and frother supplied into the chamber of the floatation machine, said flow rate of water and frother is stabilized to cause stabilization of the rate at which the source feed is delivered into the bulk of aerated pulp and, consequently, stabilization of hydrodynamic characteristics of the pulp flowing in the chamber of the floatation machine, as well as stabilization of water-to-air ratios and, in effect, the pulp density-to-level ratios in the chamber of the floatation machine.

The stabilization of the flow rate of water and frother combined with the control action of the frother flow control channel substantially improves the stabilization of the pulp density in the chamber of the floatation machine and, consequently, the pulp level stabilization.

The control action based on a change in the flow rate of water and frother is carried out jointly with the control action involving a variation of the rate of gangue discharge from the chamber of the floatation machine and the disturbing influence due to a pulp level deviation from a preset value. A pulp level variation is a disturbance necessitating a change in the flow rate of water and frother, whereas a change in the flow rate of water and frother is a disturbance necessitating a variation of the rate of gangue discharge from the chamber of the floatation machine. The pulp level, the flow rate of water and frother and the rate of gangue discharge from the chamber of the floatation machine are interrelated so that the control process ends after the pulp level in the chamber and the flow rate of water and frother reach preset values. Taking into account the fact that the pulp level control time is several times shorter than the pulp density control time in the chamber of the floatation machine there will not be any major changes in the pulp density or variations of the hydrodynamic conditions of the pulp flowing in the chamber of the floatation machine during pulp level stabilization while the flow rate of water and frother is changed.

Inasmuch as the pulp level in the chamber of the floatation machine is a priority parameter, a change in the flow rate of water and frother and subsequent stabilization of this flow rate are on the whole justified and provide for quality control of the floatation process.

The control is generally improved by enhancing accuracy in measuring the level and density of pulp in the chamber of the floatation machine. The accuracy in measuring the above parameters is increased thanks to inclusion in the pulp level and density measuring channel of hydrostatic tubes which permit measurements of the pulp level and density in increments with respect to their minimum values so as to eliminate constant components of the signals. The utilization of the hydrostatic tubes makes it possible to locate the bubbling tubes in a non-corrosive fluid supplied into the hydrostatic tubes instead of placing the bubbling tubes in the bulk of the pulp in the chamber of the floatation machine. Such an arrangement of the bubbling tubes prevents clogging of their lower portions and the associated errors in measuring the pulp level and density.

The control quality is also improved due to the use in the proposed device of an actuator valve serving to change the rate of gangue discharge from the chamber of the floatation and having an essentially linear flow characteristic. Its flow characteristic is flat due to the fact that the shut-off member has a working portion shaped as a parabolic cone. A horizontal position of the actuator valve excludes the clogging of the branch pipe used to discharge gangue from the chamber of the floatation machine in instances where the gangue contains many large and heavy fractions and appreciably decreases pulp level disturbances caused by a variation of the gangue discharge rate, a feature improving the control quality. A vertical displacement of the shut-off member of the actuator valve relative to the seat axis provides for the maximum free discharge of gangue from the chamber of the floatation machine with minimum losses of the pulp liquid phase, which enhances the pulp level stabilization.

BRIEF DESCRIPTION OF THE DRAWINGS

The invention will now be described further with reference to a specific embodiment thereof, taken in conjunction with the accompanying drawings wherein.

DETAILED DESCRIPTION OF THE INVENTION

Figure 1:
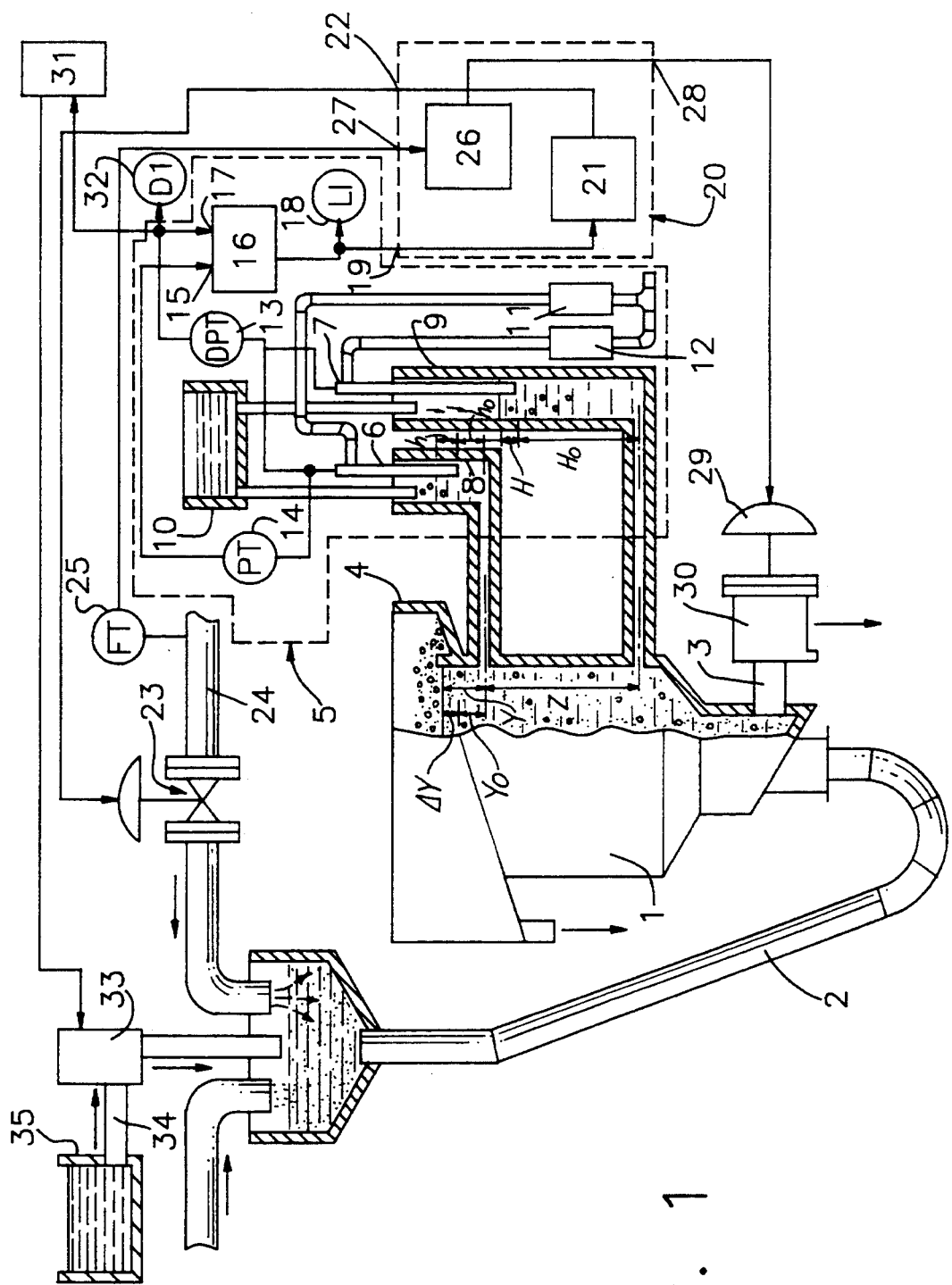
FIG. 1 is a diagrammatic general view of a floatation installation with a channel used to measure the level and density of pulp in a chamber of a floatation machine, a frother flow control channel and a channel used to stabilize the pulp level in the chamber of the floatation machine, which includes a circuit designed to control the gangue discharge rate and a circuit designed to control the flow rate of water and frother according to the invention.

The proposed device for controlling automatically the process of separating froth concentrate from gangue in a floatation machines will be described referring to, by way of example, to a floatation installation comprising a single-chamber floatation machine with the source feed representing small fractions of ore supplied on the underside into a chamber 1 (FIG. 1) over a pipeline 2.

The chamber 1 has a gangue discharge branch pipe 3 in its lower portion and a froth concentrate collection chute 4 in its upper portion. The automatic control device according to the invention comprises a channel 5 used to measure the level and density of pulp in the chamber of the floatation machine, in which two bubbling tubes 6 and 7 are placed, respectively, in hydrostatic tubes 8 and 9 communicating with the chamber 1 at different levels Y and Y+Z relative to the pulp level. The hydrostatic tubes 8 and 9 are in communication with a source 10 to fluid having a known density, as a rule, water supplied into the hydrostatic tubes 8 and 9 with a small, essentially constant flow rate which does not affect the pulp density in the chamber 1. The bubbling tubes 6 and 7 are arranged in the hydrostatic tubes 8 and 9 at different levels relative to the pulp level in the chamber 1, which define a predetermined pulp level and density measuring range. More specifically, the bubbling tube 6 is found at a level $h_o$ with respect to the level at which the hydrostatic tube 8 communicates with the chamber 1, while the bubbling tube 7 is placed at a level $H_o$ with respect to the level at which the hydrostatic tube 9 communicates with the chamber 1.

The bubbling tubes 6 and 7 are connected, respectively, with air flow governors 11 and 12 and with a differential pressure transducer 13. The bubbling tube 6 is also in communication with a pressure transducer 14 whose output is connected to a first data input 15 of a pulp level correction unit 16 comprised in the pulp level and density measuring channel 5. A second data input 17 of the correction unit 16 is connected to the output of the differential pressure transducer 13, whereas its output is connected to the input of a pulp level recorder 18 and also to an input 19 of a channel 20 used to stabilize the pulp level in the chamber of the floatation machine.

The channel 20 used to stabilize the pulp level in the chamber of the floatation machine comprises a circuit 21 designed to control the flow rate of water and frother supplied into the chamber, its input serving as the input 19 of the pulp level stabilizing channel 20, which receives a signal corresponding to an increment of the pulp level in the chamber 1, corrected with respect to density. The output of the flow control circuit 21 acts as a first output 22 of the pulp level stabilizing channel 20 and is connected to an actuator valve 23 installed on a pipeline 24 feeding water and frother to the chamber of the floatation machine. The pipeline 24 also mounts a water and frother flow transducer 25 whose output is connected to the input of a circuit 26 designed to control the rate of gangue discharge from the chamber of the floatation machine, which acts as an input 27 of the pulp level stabilizing channel 20.

The gangue discharge rate control circuit 26 is connected via its output serving as a second output 28 of the pulp level stabilizing channel 20 to a drive 29, for example, a pneumatic drive of a gangue discharge actuator valve 30 unstalled on the branch pipe 3 used to discharge gangue from the chamber of the floatation machine. The circuit 26 develops at its output a control signal in response to a deviation of the flow rate of water and frother from a preset value.

The automatic control device forming the subject of the present invention further comprises a frother flow control channel 31 connected via its input to the output of the differential pressure transducer 13 and to the input of a pulp density recorder 32 and via its output to a frother meter 33 which is connected through a pipeline 34 with a frother service tank 35 and with the pipeline 2 supplying the source feed into the chamber of the floatation machine.

In the floatation installation of FIG. 1 frother, pulp and water are mixed up directly in the pipeline 2. When the pulp is to contain other floatation reagents in addition to frother, the floatation installation may include a mixing tank to ensure contact between these reagents and the solid phase of the pulp.

The pulp level correction unit 16 comprises a first current-to-voltage converter 36 whose input serves as the input 15 of the pulp level correction unit 16 receiving a signal corresponding to a pulp level increment relative to a minimum value and a second current-to-voltage converter 37 whose input serve as the input 17 of the correction unit 16 receiving a signal corresponding to a pulp density increment relative to a minimum value. The output of the current-to-voltage converter 37 is connected to the input of a first multiplier unit 38 multiplying relevant data into a factor inversely proportional to the difference Z (FIG. 1) between the levels at which the hydrostatic tubes 8 and 9 communicate with the chamber 1 of the floatation machine. The output of a multiplier unit 38 (FIG. 2) is connected to the input of a second multiplier unit 39 multiplying relevant data into a factor proportional to a minimum value $Y_o$ (FIG. 1) of the pulp level.

The output of the current-to-voltage converter 36 (FIG. 2) is connected to one input of a first adder 40 whose other input is connected to the output of the second multiplier unit 39. The output of the first multiplier unit 38 is also connected to one input of a second adder 41 whose other input receives a signal corresponding to a minimum pulp density, its output being connected to the input of a first divider unit 42 dividing relevant data by a scale factor. The output of the first adder 40 is connected to one input of a second divider unit 43 whose other input is connected to the output of the first divider unit 42. The output of the second divider unit 43 is connected to the input of the voltage-to-current converter 44 whose output serves as the output of the pulp level correction unit 16 and is connected to that input of the pulp level recorder 18 and to the input 19 of the pulp level stabilizing channel 20.

The frother flow control channel 31 comprises a pulp density increment control 45 whose output is connected to a first input 46 of a circuit 47 for comparing a measured pulp density increment with a preset value, a second input 48 of which acts as the input of the frother flow control channel 31. The output of the comparison circuit 47 is connected to the input of an analog pulse length regulator 49 whose output is connected to a pulse length control input 50 of an automatic frother metering system 51 whose pulse frequency control input 52 is connected to the input 48 of the comparison circuit 47. The automatic frother metering system 51 develops at its output square pulses whose frequency and duration can be adjusted. This output is, at the same time, the output of the frother flow control channel 31.

In the channel 20 used to stabilize the pulp level in the chamber of the floatation machine, the circuit 21 designed to control the flow rate of water and frother supplied into the chamber comprises a pulp level increment control 53 whose output is connected to a first input 54 of a circuit 55 for comparing a corrected pulp level increment with a preset value, a second input 56 of which acts as the input 19 of the pulp level stabilizing channel 20. The output of the comparison circuit 55 is connected to the input of a water and frother flow governor 57 having its output connected to the input of an electropneumatic converter 58. The output of the electropneumatic converter 58 serves as the output of the circuit 21 designed to control the flow rate of water and frother supplied into the chamber, and also as the output 22 of the pulp level stabilizing channel 20 and is connected to an actuator valve 23 provided with a pneumatic actuating mechanism.

In the pulp level stabilizing chamber 20, the circuit 26 designed to control the rate of gangue discharge from the chamber of the floatation machine comprises a water and frother flow control 59 having its output connected to a first input 60 of a circuit 61 for comparing the measured flow rate of water and frother with a preset value, a second input 62 of which serves as the input of the discharge rate control circuit 26 and the input 27 of the pulp level stabilizing channel 20 and is connected to the output of the water and frother flow transducer 25. The output of the comparison circuit 61 is connected to the input of a governor 63 used to control the rate of gangue discharge from the chamber of the floatation machine and having its output connected to the input of an electropneumatic converter 64. The output of said electropneumatic converter serving as the output of the discharge rate control circuit 26 and the output 28 of the pulp rate stabilizing channel 20 is connected to the drive 29 of the actuator valve 30 used to discharge gangue from the chamber of the floatation machine.

Figure 3:
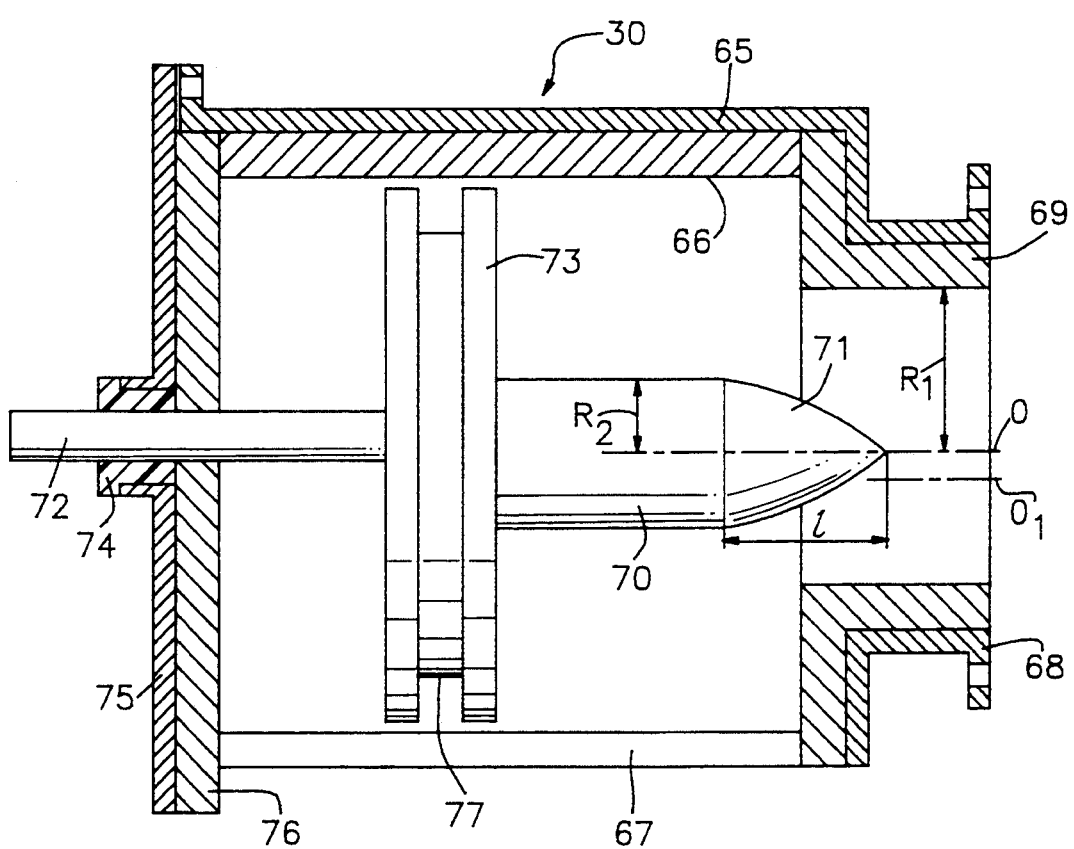
FIG. 3 is a general view of a gangue discharge actuator valve (a longitudinal section of its case) according to the invention.

The gangue discharge actuator valve 30 installed on the branch pipe 3 (FIG. 1) used to discharge gangue from the chamber of the floatation machine comprises a horizontally arranged cylindrical case 63 (FIG. 3) with a lining 66, for example, a rubber lining having a gangue discharge hole 67 in its lower portion. One of the ends of the case 65 mounts a flange 68 for connection with the discharge branch pipe 3 (FIG. 1). The case 65 (FIG. 3) mounts in its flange 68 a seat 69 made of a suitable wear-resistant material, for example, rubber. The case 65 also accommodates a shut-off member having a cylindrical portion 70 and a parabolic cone portion 71 connected therewith and facing the seat 69. The cylindrical portion 70 is rigidly connected to a rod 72 and to a pulp deflector 73 made of a suitable wear-resistant material and mounted on the end of the cylindrical portion 70. The rod 72 is placed in a plain bearing 74 located on a cover 75 of the case 65 having a lining 76, for example, a rubber lining and connected to the rod of the drive 29 (FIG. 1) of the actuator valve 30. The axis "O" (FIG. 3) of the shut-off member aligned with the axis of the case 65 is displaced upwards relative to the axis "$O_1$" of the hole in the seat 69, the eccentricity being equal to the difference between radius $R_1$ of the hole in the seat 69 and radius $R_2$ of the cylindrical portion 70 of the shut-off member. This provides for the maximum free discharge of gangue from the chamber 1 (FIG. 1) of the floatation machine with minimum losses of the liquid phase of the pulp (water and frother) and prevents the clogging of the hole in the seat 69 (FIG. 3) and the gangue discharge branch pipe 3 (FIG. 1) with foreign objects and also with discharged gangue containing many large and heavy fractions.

The cross-sectional area S of the cylindrical portion 70 (FIG. 3) of the shut-off member is defined as $$S = (1-k)S_n \qquad (1)$$

where $S_n$ = area of hole in seat 69; and
k = proportionality factor equalling minimum-to-maximum load ratio of floatation machine.

Such a relationship has been chosen to provide for agreement between the variation range of the flow section of the gangue discharge branch pipe 3 (FIG. 1) and the variation range of the initial load put on the floatation machine.

The length of the parabolic cone portion 72 (FIG. 3) of the shut-off member is equal to the maximum travel length of the drive 29 (FIG. 1) of the gangue discharge actuator valve 30. The form of the generator of the portion 71 (FIG. 3) is determined as $$S_i = \frac{l_i}{l} \cdot S \qquad (2)$$

where $S_i$ = cross-sectional area of parabolic cone portion 71 at distance i from vertex,
S = cross-sectional area of cylindrical portion 70 of shut-off member.
l = length of parabolic cone portion 71; and
$l_i$ = distance from vertex of parabolic cone portion 71 to cross-section of portion 71 at distance i from vertex.

Such a form and length of the parabolic cone portion 71 ensures an essentially linear flow characteristic of the gangue discharge actuator valve 30 (FIG. 1) and a continuous variation of the gangue discharge rate, an advantage improving quality of automatic pulp level control.

The pulp deflector 73 (FIG. 3) protects the rod 72 of the shut-off member against wear, particularly abrasive wear due to the action of pulp, thereby increasing operational reliability of the gangue discharge actuator valve 30 (FIG. 1).

The pulp deflector 73 (FIG. 3) is made as a disk having on its lateral surface an annular depression 77 used to remove the pulp penetrating through the gap between the pulp deflector 73 and the lining 66.

The afore-mentioned advantages of the gangue discharge actuator valve 30 (FIG. 1) are particularly apparent when it is used to control the rate of discharge of abrasive pulp or pulp containing a substantial proportion of large and heavy fractions.

The automatic frother metering system 51 (FIG. 2) uses circuitry widely known to those skilled in the art.

The proposed device for controlling automatically the process of separating froth concentrate from gangue in a floatation machine operates as follows.

The level and density of pulp in the chamber 1 (FIG. 1) of the floatation machine are continuously measured while froth concentrate is separated from gangue.

It is known that a variation of the level and density of pulp in the chamber of the floatation machine brings about a change in the water level in each hydrostatic tube, which is determined from the known relationship as follows:

$$\rho \cdot h = \rho_1 \cdot h_1 \qquad (1)$$

where $\rho$ = pulp density in chamber of floatation machine;
h = distance between pulp level in chamber of floatation machine and level at which hydraulic tube communicates with chamber;
$\rho_1$ = density of water (fluid) in hydrostatic tube, and
$h_1$ = water (fluid) level in hydrostatic tube.

In the proposed automatic control device the water level in the hydrostatic tube 8 is determined from the following equations;

$$Y_o \cdot \rho_o = h_o \cdot \rho_1 \qquad (4)$$

or $$(Y_o + \Delta Y)(\rho_o + \Delta \rho) = (h_o + h) \cdot \rho_1 \quad (5)$$

where
- $Y_o$ = minimum pulp level in chamber 1 of floatation machine;
- $\rho_o$ = minimum pulp density in chamber 1 of floatation machine;
- $\Delta Y$ = increment of pulp level in chamber 1 of floatation machine;
- $\Delta \rho$ = increment of pulp density in chamber 1 of floatation machine;
- $h_o$ = water level in hydrostatic tube 8 at minimum values of pulp level and density in chamber 1 of floatation machine;
- $h$ = increment of water level in hydrostatic tube 8; and
- $\rho_1$ = density of water (fluid) in hydrostatic tube 8.

The water level in the hydrostatic tube 9 is determined from the equations given below:

$$(Z + Y_o) \cdot \rho_o = H_o \cdot \rho_1 \quad (6)$$

or $$(\rho_o + \Delta \rho)(Z + Y_o + \Delta Y) = (H_o + H) \cdot \rho_1 \quad (7)$$

where
- $\rho_1$ = density of water (fluid) in hydrostatic tube 9;
- $Z$ = difference in levels at which hydrostatic tubes 8 and 9 communicate in chamber 1 of floatation machine;
- $H$ = increment of water level in hydrostatic tube 9; and
- $H_o$ = water level in hydrostatic tube 9 at minimum values of pulp level and density in chamber 1 of floatation machine.

Subtracting equation (4) from equation (5) we get $$\Delta Y (\rho_o + \Delta \rho) = h \cdot \rho_1 - Y_o \cdot \Delta \rho \quad (8)$$

Next, subtracting equation (6) from equation (7) we get $$Z \cdot \Delta \rho = Y_o \cdot \Delta \rho + \Delta Y(\rho_o + \Delta \rho) = H \cdot \rho_1 \quad (9)$$

Subtracting equation (8) from equation (9) yields $$\Delta \rho = \frac{(H - h) \rho_1}{Z} \quad (10)$$

Referring to equation (10) it is apparent that a pulp density increment in the chamber 1 of the floatation machine is proportional to the difference in increments between the water (fluid) levels in the hydrostatic tubes 9 and 8 since $Z$ and $\rho_1$ are constants.

Referring to equation (8) we obtain the following equation for determining a pulp level increment in the chamber 1 of the floatation machine, corrected with respect to density:

$$\Delta Y = \frac{h \cdot \rho_1 - Y_o \cdot \Delta \rho}{\rho_o + \Delta \rho} \quad (11)$$

In the proposed automatic control device the bubbling tube 6 is installed in the hydrostatic tube 8 at the level $h_o$, while the bubbling tube 7 is installed in the hydrostatic tube 9 at the level $H_o$.

The pressure $P_1$ in the bubbling tube 6 is computed as $$P_1 = \rho_1 \cdot h \quad (12)$$

The pressure $P_2$ in the bubbling tube 7 will be $$P_2 = \rho_1 \cdot H \quad (13)$$

Taking into account (12) and (13) equation (10) will take the form $$\Delta \rho = \frac{P_1 - P_1}{Z} \quad (14)$$

Thus, a pulp density increment in the chamber 1 of the floatation machine is proportional to the difference in pressure between the bubbling tubes 6 and 7.

Taking into account equation (12) above relation (11) will take the form $$\Delta Y = \frac{P_1 - Y_o \cdot \Delta \rho}{\rho_o + \Delta \rho} \quad (15)$$

The signals conveying information on pressure in the bubbling tubes 6 and 7 are fed to the input of the differential pressure transducer 13 wherein it is converted into a direct-current signal proportional to the pulp density increment, which is applied to the input of the pulp density recorder 32, to the input of the frother flow control channel 31 and also to the data input 17 of the pulp level correction unit 16.

The pulp level increment in the chamber 1 of the floatation machine is monitored by measuring the pressure in the bubbling tube 6 by means of the pressure transducer 14. Since the pressure $P_1$ in the bubbling tube 6 depends both on the pulp level increment $\Delta Y$ and on the pulp density increment $\Delta \rho$ in the chamber 1 of the floatation machine according to equation (15) above, the direct-current signal at the output of the pressure transducer 14 will be dependent on the above increments.

The utilization of the hydrostatic tubes 8 and 9 in the pulp level and density measuring channel 5 allows substantially increasing accuracy in measuring the pulp density and, hence, the pulp level since the measured level of the pulp is corrected with respect to its density. The pulp level and density are measured with respect to their increments over the preset minimum values below which measurements are not expedient. This permits eliminating a constant component from the measured values of the pulp level and density. The pressure transducer 14 and the differential pressure transducer 13 can, thus, be used in small pressure and, correspondingly, differential pressure variation ranges with a variation range of the output signals of the transducers 13 and 14 being essentially unchanged, a feature enhancing sensitivity and measuring accuracy of the proposed automatic control device. Referring to equations (4) through (15) it may be seen that the accuracy is increased about 9 times in pulp density measurements and about 3 times in pulp level measurements as compared with the case where the bubbling tubes 6 and 7 are placed directly in the pulp in the chamber 1. A higher accuracy in pulp level and density measurements improves such a control quality characteristic as pulp level and density control (stabilization) accuracy.

To eliminate a pulp level measurement error caused by pulp density variations in the chamber 1 of the floatation machine, a direct-current signal derived from the output of the pressure transducer 14 and corresponding to a pulp level increment over a minimum value is applied to the data input 15 of the pulp level correction unit 16, in which said signal comes to the input of the current-to-voltage converter 36 (FIG. 2), whence it is converted into a proportional d.c. voltage fed to the first input of the first adder 40. A direct-current signal corresponding to a pulp density increment over a minimum value is applied to the input of the current-to-voltage converter 37 and to the data input 17 of the pulp level correction unit 16, whence it is converted into a proportional d.c. voltage fed to the input of the first multiplier unit 38. The multiplier unit 38 multiplies said voltage signal into a factor inversely proportional to the difference Z (FIG. 1) between levels at which the hydrostatic tubes 8 and 9 communicate with the chamber 1 of the floatation machine. The d.c. voltage signal is then applied from the output of the multiplier unit 38 (FIG. 2) to the input of the second multiplier unit 39 wherein it is multiplied into a factor proportional to the minimum value $Y_o$ (FIG. 1) of the pulp level in the chamber 1 of the floatation machine. Thereafter the d.c. voltage signal is fed from the output of the second multiplier unit 39 (FIG. 2) to the second input of the first adder 40 which subtracts said voltage from the voltage applied to the first input of the adder 40. At the same time, the d.c. voltage signal derived from the output of the first multiplier units 38 is applied to one of the inputs of the second adder 41 whose other input receives a d.c. voltage signal proportional to the minimum pulp density $\rho_o$. As a result, the d.c. voltage at the output of the second adder 41 will be equal to a sum of said voltages and fed to the input of the first divider unit 42. The first divider unit 42 divides said voltage by a scale factor. A differential voltage signal derived from the output of the first adder 40 is fed to one of the inputs of the second divider unit 43 whose other input receives d.c. voltage from the output of the first divider unit 42. As a result, the second divider unit 43 will have at its output d.c. voltage proportional to the ratio of said voltages, which is applied to the input of the voltage-to-current converter 44 whence it is converted into direct current and fed to the input of the pulp level recorder 18 and to the input 19 of the pulp level stabilizing channel 20.

When froth concentrate is separated from gangue in a floatation machine, there occurs interrelated control of such parameters as the level and density of pulp in the chamber 1 (FIG. 1) of the floatation machine, as well as the flow rate of water and frother supplied into the chamber 1 of the floatation machine.

In this case interrelated control involves considerable difficulties due to a change in residual concentration of frother in circulating water supplied into the chamber 1 of the floatation machine while froth concentrate is separated from gangue in the chamber 1 of the floatation machine. This causes a change in the density of pulp in the chamber 1 and necessitates control of the flow rate of frother fed to the chamber 1 of the floatation machine to restore the pulp density and ensure separation of froth concentrate from gangue in the chamber 1 of the floatation machine. A variation of the pulp density causes an additional change in the pulp level in the chamber 1 of the floatation machine. The pulp level in the chamber 1 is a priority parameter since its increase results in contamination of froth concentrate with gangue and impairs the conditions of extracting a useful constituent from the source feed supplied into the froth layer due to the fact that the position of the froth layer changes, while its decrease leads to a lower yield of froth concentrate and losses of the useful constituent due to untimely delivery of froth concentrate into the collection chute 4 whereby the useful constituent will settle on the bottom of the chamber 1 of the floatation machine. Therefore, the proposed device for controlling automatically the process of separating froth concentrate from gangue in a floatation machine is designed so that the pulp level is stabilized both by governing the rate of gangue discharge from the chamber 1 of the floatation machine and controlling the flow rate of water and frother supplied into the chamber 1 of the floatation machine with subsequent stabilization of the flow rate of water and frother to ensure indirect stabilization of the pulp density in the chamber 1 of the floatation machine.

The flow rate of frother is controlled by the frother flow control channel 31 whose input receives a current signal from the output of the differential pressure transducer 13, which is proportional to a pulp density increment in the chamber 1 of the floatation machine. The frother flow control channel 31 furnishes an output signal representing direct-current pulses varying in frequency and duration and applied to the frother meter 33 which operates causing frother portions to enter the chamber 1 of the floatation machine. In the frother flow control channel 31, a direct-current signal proportional to a pulp density increment is fed to the pulse frequency control input 52 (FIG. 2) of the automatic frother metering system 51 and also to the input 48 of the circuit 47 for comparing a measured pulp density increment with a preset value, the input 46 of said circuit receiving a direct-current signal from the pulp density increment control 45.

When the signals indicative of the measured and preset pulp density increments are equal, their differential signal at the output of the comparison circuit 47 is zero. The analog pulse length regulator 49 produces a direct-current signal having a constant magnitude and applied to the pulse length control input 50 of the automatic frother metering system 51. The output signal of this system represents square direct-current pulses whose frequency is proportional to the direct-current signal at the input 52 of the system 51, while their duration is proportional to the direct-current signal at its input 50. The square direct-current pulses derived from the output of the automatic frother metering system 51 are fed to the input of the frother meter 33 which operates causing frother portions to enter the chamber 1 (FIG. 1) of the floatation machine.

Figure 2:
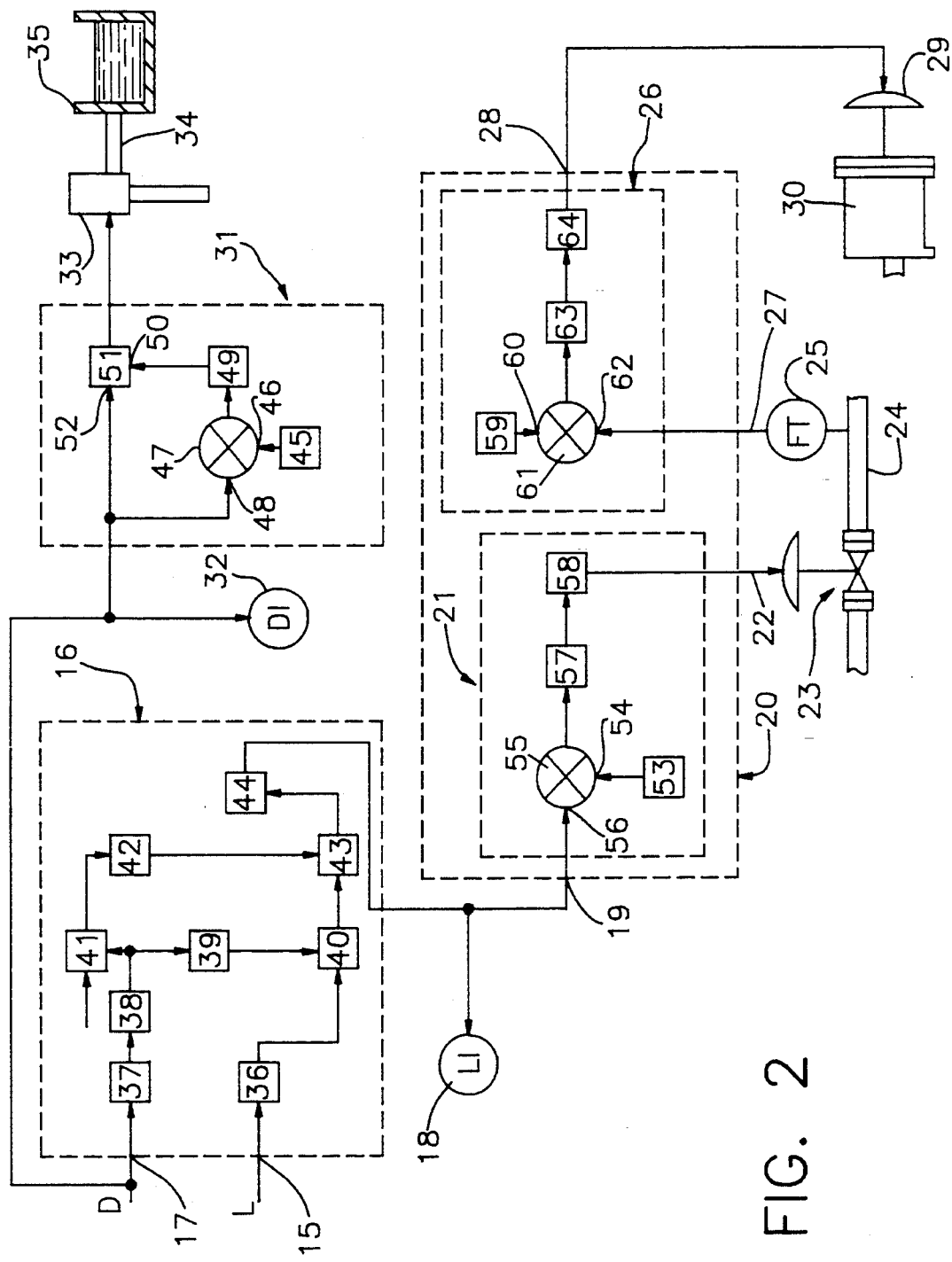
FIG. 2 is a block diagram showing a pulp level correction unit, the frother flow control channel and the pulp level stabilizing channel according to the invention.

A rise or fall of the signal proportional to a pulp density increment causes a corresponding increase or decrease in the frequency of the output pulses of the automatic frother metering system 51 (FIG. 2). At the same time, the comparison circuit 47 develops at its output a direct-current signal indicative of the difference between the signal proportional to the measured pulp density increment and the signal of the pulp density increment control 45. Thereafter the differential signal is applied to the input of the analog pulse length regulator 49 whose output signal increases or decreases due to the proportional-plus-integral control action. Next, the output signal of the analog pulse length regulator 49 is applied to the pulse length control input 50 of the automatic frother metering system 51 due to which the duration of the output square direct-current pulses will increase or decrease. Thus, the frequency and duration of the direct-current pulses at the output of the automatic frother metering system 51 will increase or decrease, a factor causing a corresponding increase or decrease in the supply of frother to the chamber 1 (FIG. 1) of the floatation machine. A change in the frother supply will bring about a corresponding variation of frother concentration in the pulp fed over the pipeline 2 to the chamber 1 of the floatation machine and, consequently, a variation of the pulp density in the chamber 1. The flow rate of frother will change until the pulp density increment equals a preset value.

As froth concentrate is separated from gangue, the pulp level in the chamber 1 of the floatation machine is stabilized through the pulp level stabilizing channel 20 whose input 19 receives a direct-current signal proportional to a corrected pulp level increment in the chamber 1 of the floatation machine, said signal being derived from the output of the pulp level correction until 16. At the same time, the input 27 of the pulp level stabilizing channel 20 receives a direct-current signal from the output of the transducer 25 indicative of the flow rate of water and frother supplied into the chamber 1 of the floatation machine through the pipeline 24. The pulp level stabilizing channel 20 gives two control actions. The first action is produced at the output 22 of the pulp level stabilizing channel 20 by the circuit 21 designed to control the flow rate of water and frother supplied into the chamber. The second action is produced at the output 28 of the pulp level stabilizing channel 20 by the gangue discharge rate control circuit 26. The channel 20 used to stabilize the pulp level in the chamber of the floatation machine is designed so that the control of the process stops only when the pulp level increment in the chamber 1 of the floatation machine and the flow rate of water and frother supplied into the chamber 1 of the floatation machine reach preset values.

In the channel 20 used to stabilize the pulp level in the chamber of the floatation machine, a direct-current signal proportional to a corrected pulp level increment in the chamber 1 is fed to the input 56 (FIG. 2) of the circuit 55 for comparing a corrected pulp level increment with a preset value, the input 54 of said circuit receiving a direct-current signal from the pulp level increment control 53. When the signal of the pulp level increment control 53 and the signal corresponding to a corrected pulp level increment and fed to the input 56 of the comparison circuit 55 are equal, the output signal of said comparison circuit is zero. The output signal of the comparison circuit 55 is fed to the input of the analog water and frother flow governor 57 which furnishes a direct-current signal having a constant magnitude and applied to the input of the electropneumatic converter 58, whence it is converted into a proportional pneumatic signal. Thereafter said signal is fed to the actuator valve 23 provided with a pneumatic actuating mechanism and arranged on the pipeline 24. The actuator valve 23 passes water and frother into the chamber 1 (FIG. 1) of the floatation machine. The pipeline 24 mounts the water and frother flow transducer 25 developing at its output a direct-current signal proportional to the flow rate of water and frother supplied via the pipeline 24 into the chamber 1 of the floatation machine. The output signal of the water and frother flow transducer 25 is applied to the input 62 (FIG. 2) of the circuit 61 for comparing the measured flow rate of water and frother with a preset value, the other input 60 of said comparison circuit receiving a direct-current signal from the water and frother flow control 59. When the above signals are equal, the output signal of the comparison circuit 61 is zero. The output signal of the comparison circuit 61 is applied to the input of the analog governor 63 used to control the rate of gangue discharge from the chamber of the floatation machine, which furnishes a direct-current signal having a constant magnitude and fed to the input of the electropneumatic converter 64, whence it is converted into a proportional pneumatic signal. Next, said signal is applied to the pneumatic drive 29 of the actuator valve 30 used to discharge gangue from the chamber of the floatation machine. Gangue discharge from the chamber 1 (FIG. 1) of the floatation machine is accomplished through the actuator valve 30.

As the pulp level in the chamber 1 of the floatation machine increases or decreases, there occurs a rise or fall of the signal at the input 56 (FIG. 2) of the circuit 55 for comparing a corrected pulp level increment with a preset value. The comparison circuit 55 produces at its output a direct-current signal equal to the difference between the signal of the pulp level increment control 53 and the signal corresponding to a corrected pulp level increment and fed to the input of the water and frother flow governor 57. The direct-current signal at the output of said governor decreases or increases due to the proportional-plus-integral control action and is fed to the input of the electropneumatic converter 58 wherein it is converted into a proportional pneumatic signal. Next, said signal is applied to the actuator valve 23. As a result, the flow rate of water and frother supplied through the actuator valve 23 into the chamber 1 (FIG. 1) of the floatation machine decreases or increases, which partially compensates for an increase or decrease in the pulp level in the chamber 1 of the floatation machine.

As the flow rate of water and frother decreases or increases, there occurs a fall or rise of the direct-current signal at the output of the water and frother flow transducer 25, which is fed to the input 62 (FIG. 2) of the circuit 61 for comparing the measured flow rate of water and frother with a preset value. The latter circuit develops at its output a signal representative of the difference between the signal of the water and frother flow control 59 and the signal corresponding to the measured flow rate of water and frother. Next, the differential signal is fed to the input of the analog governor 63 used to control the rate of gangue discharge from the chamber of the floatation machine, the output signal of said governor decreasing or increasing due to the proportional-plus-integral control action. Said output direct-current signal is applied to the input of the electropneumatic converter 64 wherein it is converted into a proportional pneumatic signal. Thereafter said signal is applied to the pneumatic drive 29 of the actuator valve 30 used to discharge gangue from the chamber of the floatation machine. The drive 29 moves, in proportion to said pneumatic signal, its rod and, consequently, the rod 72 (FIG. 3) of the gangue discharge actuator valve 30 whereby the shut-off member of the actuator valve 30 will move relative to the seat 69. This causes a linear increase or decrease in the flow section of the hole in the seat 69 of the actuator valve 30 used to discharge gangue from the chamber of the floatation machine, a factor causing an increase or decrease in the rate of gangue discharge from the chamber 1 (FIG. 1) of the floatation machine and restoration of the preset pulp level in the chamber 1 of the floatation machine.

At the moment when the pulp level in the chamber 1 of the floatation machine reaches a preset value, the flow rate of water and frother supplied into the chamber 1 may differ from the rating. An error signal derived from the output of the circuit 61 (FIG. 2) for comparing the measured flow rate of water and frother with a preset value is applied to the input of the analog governor 63 used to discharge gangue from the chamber of the floatation machine, said governor continuing to generate a control signal, which finally causes a decrease or increase in the rate of gangue discharge from the chamber 1 (FIG. 1) of the floatation machine. The latter factor leads to a minor deviation of the pulp level in the chamber 1 of the floatation machine, which in turn causes a change in the flow rate of water and frother supplied into the chamber 1 of the floatation machine.

Thus, the flow rate of water and frother supplied into the chamber 1 of the floatation machine and the rate of gangue discharge from the chamber 1 of the floatation machine will be adjusted until the pulp level in the chamber 1 and the flow rate of water and frother supplied into the chamber 1 of the floatation machine reach preset values.

To avoid system driving during the control procedure, the analog governors 57 (FIG. 2) and 63 have different control features, more specifically, the analog governor 63 is characterized by a smaller gain and a greater integration time as compared with the analog governor 57.

Such a structure of the proposed device for controlling automatically the process of separating froth concentrate from gangue in a floatation machine and the utilization of a gangue discharge actuator valve having a linear flow characteristic make it possible to improve quality of automatic control, more particularly, to decrease maximum deviation of the pulp level and density from preset values during the control procedure, to reduce control time and fluctuations of the level and density of pulp in the chamber of the floatation machine, and to enhance accuracy in controlling the pulp level and density due to more accurate measurements in the pulp level and density measuring channel.

What is claimed is:

1. A flotation control apparatus comprising:

a flotation machine having a pulp filled chamber, said machine being provided with a gangue discharge branch pipe, a source feed pipeline, a frother meter means for feeding a frother and a pipeline means for feeding water-and-frother;

means for measuring the level and density of the pulp in said chamber of the flotation machine, said means for measuring having first and second outputs;

said means for measuring the level and density of the pulp further comprises:

a. first and second hydrostatic tubes installed outside said chamber of the flotation machine and connected to the chamber at different levels relative to the pulp level;

b. means for feeding a liquid at an essentially constant flow rate to each of the hydrostatic tubes, said liquid having a known constant density;

c. first and second bubbling tubes placed in the hydrostatic tubes at different levels relative to the pulp level, which define a predetermined pulp level and density range;

d. first and second air flow governor means connected to the first and second bubbling tubes, respectively, for controlling the flow rate of air to each bubbling tube;

e. a differential pressure transducer means connected with the first and second bubbling tubes and having an output serving as the first output of the pulp and density measuring means, which produces a signal corresponding to a pulp density increment;

f. a pressure transducer detecting means connected with the first bubbling tube and having an output;

g. a pulp level correction means having first and second data inputs and connected via said first and second data inputs to the outputs of said pressure transducer detecting means and said differential pressure transducer means, respectively, said correction means having an output which serves as said second output of said pulp level and density measuring means, said second output produces a signal corresponding to a value of pulp level increment corrected with respect to density;

means for controlling the flow rate of frother supplied to said chamber of the flotation machine comprising an input and an output, said means for controlling the flow of frother being connected via said input to the first output of said pulp level and density measuring means and via said output to said frother metering means;

means for stabilizing the pulp level in said chamber of the flotation machine, comprising first and second inputs and first and second outputs, a first circuit means for controlling the flow rate of water-and-frother supplied into the chamber, said first circuit means having an input serving as the first input of the pulp level stabilizing means, said first input being connected being connected to the second output of the pulp level and density measuring means, said first circuit means having an output serving as the first output of the pulp level stabilizing means; a second circuit means for controlling the rate of gangue discharged from the chamber of the flotation machine, said second circuit means having an input and an output serving, respectively, as the second input and second output of said pulp level stabilization means;

a water-and-frother valve means installed on said pipeline for controlling the flow rate of water-and-frother to the chamber of the flotation machine, having an input connected to the first output of the pulp level and stabilization means, which produces a first control signal in responce to a deviation of pulp level increment from a preset value;

a gangue discharge valve means used to discharge gangue installed on said branch pipe for discharging gangue from the chamber of the flotation machine;

a drive means for actuating said gangue discharge valve means, having an input connected to the second output of the pulp level stabilization means; and a water-and-frother flow transducer means installed on said pipeline for feeding water-and-frother and having an output connected to the second input of the pulp level stabilization means, said pulp level and stabilization means develops at its second output a second control signal fed to the drive means of the gangue discharge valve means in responce to a deviation of flow rate of water-and-frother from a preset value.

2. A flotation control apparatus as claimed in claim 1 in which said pulp level correction means comprises:

a first current-to-voltage converter means having an input serving as the first data input of said correction unit and receiving a signal corresponding to a pulp level increment over a minimum value, and an output;

a second current-voltage converter having an input serving as the second data input of said correction means and receiving a signal corresponding to a pulp density increment over a minimum value, and an output;

a first multiplier means having an input connected to said output of the second current-to-voltage converter means and an output, and said first multiplying means multiplying the input data into a factor inversely proportional to the difference between the levels at which the first and second hydrostatic tubes connect with said chamber of the floatation machine;

a second multiplier means having an input connected to said output of the first multiplier unit and an output, and said second multiplying means multiplying the input data into a factor proportional to a minimum pulp level;

a first adder means having first and second inputs and an output and connected via the first input to said output of the first current-to-voltage converter and via the second input to said output of the second multiplier;

a second adder means having first and second inputs and an output, connected via the first input to said output of the first multiplier means and receiving at the second input a signal corresponding to a minimum pulp density;

a first divider means having an input connected to said output of the second adder means and an output, and dividing the input data by a scale factor;

a second divider means having first and second inputs and an output and connected via the first and second inputs to said outputs of the first adder means and the first divider means; and a voltage-to-current converter means having an input connected to said output of the second divider means and an output acting as said output of said correction means.

3. A flotation control apparatus as claimed in claim 1 in which said first circuit means designed to control the flow rate of water-and-frother supplied into the chamber comprises:

a comparing circuit means for comparing a corrected value of pulp level increment with a preset value, said comparing circuit means having a first input serving as said input of said first circuit means, a second input and an output;

a pulp level increment control means having an output connected to the second input of said comparison circuit means;

a water-and-frother flow governor means having an input connected to said output of said comparison circuit means and an output serving as said output of said first circuit means, which produces the first control signal of said pulp level stabilizing means.

4. A flotation control apparatus as claimed in claim 1 in which the gangue discharge valve means comprises:

a cylindrical case disposed in a substantially horizontal position;

an outlet provided in the lower portion of said cylindrical case;

a flange arranged on one of the ends of said cylindrical case and connected with said branch pipe used to discharge gangue from the chamber of the flotation machine;

a seat contained within said cylindrical case; a hole defining an axis in said seat;

a shut-off member installed in said cylindrical case; said shut-off member comprising a cylindrical portion and a parabolic cone portion connected therewith and facing said seat;

a rod means connected with said drive means of the gangue discharge valve means and linked with said cylindrical portion of the shut-off member; and said shut-off member having an axis misaligned relative to the axis of said hole in said seat towards the upper portion of said cylindrical case.

5. A flotation control apparatus as claimed in claim 2 in which said first circuit means designed to control the flow rate of water-and-frother supplied into the chamber comprises:

a comparing circuit means for comparing a corrected value of pulp level increment with a preset value, said comparing circuit means having a first input serving as said input of said first circuit means, a second input and an output;

a pulp level increment control means having an output connected to the second input of said comparison circuit means;

a water-and-frother flow governor means having an input connected to said output of said comparison circuit means and an output serving as said output of said first circuit means, which furnishes the first control signal of said pulp level stabilizing means.

6. A flotation control apparatus as claimed in claim 2 in which the gangue discharge actuator valve means comprises:

a cylindrical case disposed in a substantially horizontal position;

an output provided in the lower portion of said cylindrical case;

a flange arranged on one of the ends of said cylindrical case and connected with said branch pipe used to discharge gangue from the chamber of the flotation machine;

a seat contained within said cylindrical case; a hole defining an axis in said seat;

a shut-off member installed in said cylindrical case; said shut-off member comprising a cylindrical portion and a parabolic cone portion connected therewith and facing said seat;

a rod means connected with said drive means of the gangue discharge valve means and linked with said cylindrical portion of the shut-off member; and said shut-off member having an axis misaligned relative to the axis of said hole in said seat towards the upper portion of said cylindrical case.

7. A flotation control apparatus as claimed in claim 3 in which the gangue discharge actuator valve means comprises:

a cylindrical case disposed in a substantially horizontal position;

an outlet provided in the lower portion of said cylindrical case;

a flange arranged on one of the ends of said cylindrical case, connected with said branch pipe used to discharge gangue from the chamber of the flotation machine;

a seat contained within said cylindrical case, a hole defining an axis in said seat;

a shut-off member installed in said cylindrical case; said shut-off member comprising a cylindrical portion and a parabolic cone portion connected therewith and facing said seat;

a rod means connected with said drive means of the gangue discharge valve means and linked with said cylindrical portion of the shut-off member; and said shut-off member having an axis misaligned relative to the axis of said hole in said seat towards the upper portion of said cylindrical case.

8. A flotation control apparatus as claimed in claim 4 in which the cross-sectional area of said cylindrical portion of said shut-off member is determined from the equation $$S = (l-k)S_n$$

where

S is the cross-sectional area of said cylindrical portion;

$S_n$ is the area of said hole in said seat; and k is a proportionality factor equalling a minimum-to-maximum load ratio of the flotation machine, the length of said parabolic cone portion being equal to the travel length of said drive means of the gangue discharge valve means.

9. A flotation control apparatus as claimed in claim 4, comprising pulp deflector means disposed on the end of said cylindrical portion of said shut-off member and serving to link the shut-off member and said rod means.

10. A flotation control apparatus as claimed in claim 6 in which the cross-sectional area of said cylindrical portion of said shut-off member is determined from the equation $$S = (l-k)S_n$$

where

S is the cross-sectional area of said cylindrical portion;

$S_n$ is the area of said hole in said seat; and k is a proportionality factor equalling a minimum-to-maximum load ratio of the flotation machine, the length of said parabolic cone portion being equal to the travel length of said drive means of the gangue discharge valve means.

11. A flotation control apparatus as claimed in claim 6, comprising a pulp deflector means disposed on the end of said cylindrical portion of said shut-off member and serving to link the shut-off member and said rod means.

12. A flotation control apparatus as claimed in claim 7 in which the cross-sectional area of said cylindrical portion of said shut-off member is determined from the equation $$S = (l-k)S_n$$

where

S is the cross-sectional area of said cylindrical portion;

$S_n$ is the area of said hole in said seat; and k is a proportionality factor equalling a minimum-to-maximum load ratio of the flotation machine, the length of said parabolic cone portion being equal to the travel length of the drive means of the gangue discharge valve means.

13. A flotation control apparatus as claimed in claim 7, comprising pulp deflector means disposed on the end of said cylindrical portion of said shut-off member and serving to link the shut-off member and said rod means.

14. A flotation control apparatus as claimed in claim 8 in which said misalignment of the axis of said shut-off member relative to the axis of said hole in said seat is equal to the difference between radii of the cylindrical portion and said hole.

15. A flotation control apparatus as claimed in claim 9, wherein said pulp deflector means comprises a disk having an annular depression on its lateral surface.

16. A flotation control apparatus as claimed in claim 10 in which said misalignment of the axis of said shut-off member relative to the axis of said hole in said seat is equal to the difference between radii of said cylindrical portion and said hole.

17. A flotation control apparatus as claimed in claim 11, wherein said pulp deflector means comprises a disk having an annular depression on its lateral surface.

18. A flotation control apparatus as claimed in claim 12 in which said misalignment of the axis of said shut-off member relative to the axis of said hole in said seat is equal to the difference between radii of said cylindrical portion and said hole.

19. A flotation control apparatus as claimed in claim 13, wherein said pulp deflector means comprises a disk having an annular depression on its lateral surface.

* * * * *